United States Patent
Rowland

(10) Patent No.: US 10,563,145 B2
(45) Date of Patent: Feb. 18, 2020

(54) ALKYLATED 3-HYDROXYDIPHENYLAMINE ANTIOXIDANTS

(71) Applicant: LANXESS Solutions US Inc., Middlebury, CT (US)

(72) Inventor: Robert G. Rowland, Woodbridge, CT (US)

(73) Assignee: LANXESS Solutions US Inc., Shelton, CT (US)

( * ) Notice: Subject to any disclaimer, the term of this patent is extended or adjusted under 35 U.S.C. 154(b) by 0 days.

(21) Appl. No.: 15/703,397

(22) Filed: Sep. 13, 2017

(65) Prior Publication Data

US 2018/0079985 A1    Mar. 22, 2018

Related U.S. Application Data

(60) Provisional application No. 62/396,887, filed on Sep. 20, 2016, provisional application No. 62/463,839, filed on Feb. 27, 2017.

(51) Int. Cl.
| | |
|---|---|
| *C10M 133/54* | (2006.01) |
| *C10M 169/04* | (2006.01) |
| *C10M 133/14* | (2006.01) |
| *C10M 105/00* | (2006.01) |
| *C07C 215/82* | (2006.01) |
| *C07C 211/57* | (2006.01) |
| *C07C 211/55* | (2006.01) |

(52) U.S. Cl.
CPC ......... *C10M 133/54* (2013.01); *C07C 211/55* (2013.01); *C07C 211/57* (2013.01); *C07C 215/82* (2013.01); *C10M 105/00* (2013.01); *C10M 133/14* (2013.01); *C10M 169/04* (2013.01); *C07C 2602/10* (2017.05); *C10M 2203/003* (2013.01); *C10M 2207/026* (2013.01); *C10M 2215/062* (2013.01); *C10M 2215/064* (2013.01); *C10M 2215/26* (2013.01); *C10N 2230/04* (2013.01); *C10N 2230/08* (2013.01); *C10N 2230/10* (2013.01); *C10N 2240/10* (2013.01)

(58) Field of Classification Search
CPC combination set(s) only.
See application file for complete search history.

(56) References Cited

U.S. PATENT DOCUMENTS

| | | | |
|---|---|---|---|
| 2,369,075 A | 2/1945 | Robbins | |
| 3,751,472 A | 8/1973 | Wheeler | |
| 3,781,203 A | 12/1973 | Braid | |
| 5,338,885 A | 8/1994 | Immel et al. | |
| 5,449,829 A | 9/1995 | Kusuda et al. | |
| 6,599,865 B1 | 7/2003 | Esche, Jr. et al. | |
| 7,498,467 B2 | 3/2009 | Shiraki | |
| 7,501,386 B2 | 3/2009 | Cherpeck et al. | |
| 7,569,526 B2 | 8/2009 | Costello et al. | |
| 7,704,931 B2 | 4/2010 | Dong et al. | |
| 7,838,703 B2 | 11/2010 | Ma et al. | |
| 8,202,829 B2 | 6/2012 | Devlin et al. | |
| 2007/0082828 A1 | 4/2007 | Nalesnik | |
| 2007/0142243 A1 | 6/2007 | Cherpeck et al. | |
| 2007/0203035 A1 | 8/2007 | Dong et al. | |
| 2007/0293408 A1* | 12/2007 | Opstal | C10M 169/04 508/471 |
| 2011/0237474 A1* | 9/2011 | Mazzamaro | C10M 141/08 508/364 |

FOREIGN PATENT DOCUMENTS

| | | |
|---|---|---|
| EP | 0165559 A1 | 12/1985 |
| GB | 1145189 A | 3/1969 |
| JP | 2011-256314 A | 12/2011 |
| WO | 2009067315 A1 | 5/2009 |
| WO | 2012/146530 A1 | 11/2012 |

OTHER PUBLICATIONS

Kyazim-Zade et al., Neftekhimiya (1996), 36(1), 73-75, Abstract only.
PCT International Search Report and Written Opinion dated Dec. 8, 2017 from corresponding Application No. PCT/US2017/051335, 14 pages.
Poliak et al., Polymer Degradation and Stability (2015) 114, 34-44.
Zhang et al., Organic Letters, 15(8), 2018-2021, 2013, XP002775496 Abstract.
Janik et al., Physica (Amsterdam), 77(3), 514-22, 1974, XP002775497 Abstract.
Jancevska-Ni Kolovska, Rad Jugoslavenske Akademije Znanosti I Umjetnosti, 398, 93-101, 1983, XP002775498 Abstract.
Soulie, Tetrahedron, 57 (6), 1035-1040, 2001 XP002775499 Abstract.
Zhang et al., Journal of the American Chemical Society, 134(12), 5492-5495, XP002775500 Abstract.
Lubricant Additives Chemistry and Applications, 2nd Ed., Leslie Rudnick, 4-43 (2009).
Lubricant Additives, Vanderbilt Worldwide Ltd. (2015).

\* cited by examiner

*Primary Examiner* — Ellen M McAvoy
*Assistant Examiner* — Chantel L Graham

(57) ABSTRACT

Certain alkylated 3-hydroxyphenylamine antioxidants wherein one phenyl is substituted by at least one hydroxyl group at the 3-position relative to the amine and the other phenyl is substituted by at least one substituent having 4 or more carbon atoms are surprisingly effective antioxidants, especially in lubricating oils.

20 Claims, No Drawings

ALKYLATED 3-HYDROXYDIPHENYLAMINE ANTIOXIDANTS

Provided are alkylated 3-hydroxyphenylamine antioxidants wherein one of the phenyl rings is substituted by at least one hydroxyl group at the 3-position relative to the amine and the other phenyl is substituted by at least one substituent having 4 or more carbon atoms, and lubricating oil compositions comprising a lubricating oil and said alkylated 3-hydroxydiphenylamine antioxidants.

BACKGROUND

Lubricants are often used in demanding environments where degradation can be accelerated by high temperatures, extreme wear conditions, acidic or other corrosive conditions, etc. For example, the conditions under which automobile engines function are severe enough to require periodic oil changes to replace degraded engine lubricant in order to protect the engine against wear and damage that can lead to catastrophic failure.

Alkylated diaryl amines, such as alkylated diphenylamines (ADPAs), are well known antioxidants widely used to prevent degradation and maintain the performance of engine oils found in gasoline and diesel engines for cars and trucks, as well as a variety of industrial lubricants and lubricants for marine engines, etc. When selecting a diaryl amine antioxidant a number of performance, safety and environmental concerns must be addressed. For example, diphenylamine itself has good antioxidant activity but is known to be a sensitizer and its presence is typically kept to a minimum, e.g., less than 1% of any ADPA antioxidant. Diphenylamines substituted with hydrocarbyl groups are more soluble in lubricating oil and the higher molecular weight reduces volatility. Increased alkylation also helps to solubilize polar materials formed from oligomerization of spent oxidized amines, which reduces deposits, sludge and varnish. On the other hand, the antioxidant activity of ADPAs is dependent on the concentration of nitrogen provided and is thus inversely proportional to molecular weight and so excessive alkylation or very large alkyl groups should be avoided. NAUGALUBE 438L, a mixture of diphenylamines alkylated by one or more nonyl-chains derived from propylene trimer is an effective and widely used liquid antioxidant.

Diaryl amines useful as anti-oxidants bearing substituents other than alkyl groups are known but such compounds are not as common in engine oils as alkyl substituted diaryl amines. For example, U.S. Pat. No. 7,704,931 includes 3-hydroxydiphenylamine and 4-hydroxydipenylamine in lists of possible antioxidants in a lubricant composition; U.S. Pat. No. 8,202,829 includes 3-hydroxydiphenylamine in a list of suitable antioxidants for use in a non-synthetic lubricating oil comprising less than 30 wt % monocycloparaffins and from 0.8 to 2.0 wt % tetracycloparaffins; and U.S. Pat. No. 7,569,526 includes 3-hydroxydiphenylamine and 4-hydroxydipenylamine in lists of possible antioxidants for use in the oil portion of a metal working fluid, but none of these three disclosures exemplify the use of a hydroxydiphenylamine.

U.S. Pat. No. 7,498,467 disclose aminophenol and hydroxydiphenylamine antioxidants wherein on at least one phenyl ring a hydroxyl substituent is adjacent to an amino substituent.

JP 2011-256314 discloses a composition comprising an aliphatic alkyl ester biodiesel fuel, which fuel may also contain a fossil fuel component, and an antioxidant of the formula

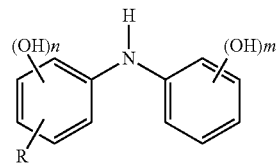

wherein n and m can be 0, 1 or 2 provided that m+n=1 or 2, and R is a C1-18 alkyl, which alkyl may be further substituted. Of the possible hydroxydiphenyl amine compounds of the above formula, only 4-hydroxydiphenylamine is exemplified.

GB 1,145,189 discloses the use of substituted 2-hydroxydiphenylamines as antioxidants in hydrocarbon and ester based lubricating oils.

EP 016559 discloses 3-hydroxy-4-styryldiphenylamine, which may also be further substituted by styryl at the 2- or 4'-positions, as an antioxidant for hydrocarbon and ester based lubricating oils. Compositions comprising ester based oils are exemplified.

"Thermoanalytic study of inhibitors of oxidation of synthetic oils" Kyazim-zade, A. K.; Gadirov, A. A.; Akchurina, T. Kh., Neftekhimiya (1996), 36(1), 73-75 investigated the thermal stability and the effect on the oxidation of pentaerythritol esters at elevated temperatures of certain 3-hydroxyl or 3-alkoxy-4-hexyldiarylamines of the following formula:

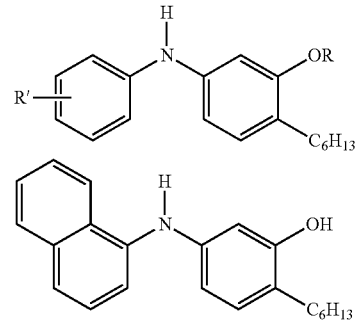

wherein R is hydrogen, butyl or hexyl and R' is hydrogen or methyl.

There is some suggestion in the literature that substitution with a hydroxyl group at the 2 and 4 positions of a diphenyl amine would lead to increased antioxidant activity, but hydroxyl substitution at the 3 positions is not expected to provide the same benefit, as discussed in, for example, "Substitution and torsional effects on the energetics of homolytic N—H bond cleavage in diphenylamines" Poliak, Peter; Vaganek, Adam; Lukes, Vladimir; Klein, Erik, Polymer Degradation and Stability (2015) 114, 34-44.

It has been found that certain alkylated 3-hydroxydiphenylamines, i.e., diphenylamines substituted on one phenyl ring by at least one hydroxyl at the 3-position relative to the amino group and substituted on the other phenyl by at least one group having 4 or more carbon atoms, provide excellent oxidation protection and deposit control for lubricants, such as lubricating oils used in automobile engines, truck engines, wind turbines, etc. In many embodiments, the alkylated 3-hydroxydiphenylamine antioxidants of the invention provide greater anti-oxidant and/or deposit control activity than hydroxydiphenylamines substituted by hydroxyl at the 2- and/or 4-position rather than the 3-position. Particularly good performance is seen when the alkylated 3-hydroxydiarylamines are used in combination with alkylated diarylamines, such as commercially available products like nonylated diphenylamine NAUGALUBE 438L.

SUMMARY

The present invention provides alkylated hydroxydiphenylamines of formula I, and lubricating oil compositions comprising them;

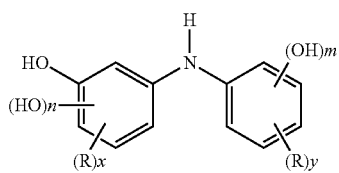

wherein n is 0 or 1; m is 0, 1 or 2; e.g., n is 0 and m is 0 or 1;

x is 0, 1 or 2 and y is 1, 2 or 3; e.g., x is 0 or 1 and y is 1 or 2;

each R is independently $C_{4-24}$, $C_{4-18}$ or $C_{4-12}$ alkyl, $C_{7-18}$ aralkyl, or $C_{4-24}$, $C_{4-18}$ or $C_{4-12}$ alkyl substituted by one or more hydroxyl and/or interrupted by one or more oxygen atom, or two adjacent R groups together with the carbons to which they are attached form a 5 to 8 member heterocyclic ring or a 6 to 8 member non-aromatic carbocyclic ring, which heterocyclic or non-aromatic carbocyclic ring is optionally substituted by alkyl, e.g., $C_{1-4}$ alkyl, hydroxyl or alkoxy;

and wherein at least one carbon atom adjacent to the amine nitrogen is unsubstituted, i.e., is substituted by hydrogen.

In the present disclosure, the article "a" or "an" in relation to component means "one or more than one", unless otherwise specified.

In certain embodiments, the alkylated 3-hydroxydiphenylamine of the invention is used in combination with hydroxydiarylamines substituted by hydroxyl at the 2- and/or 4-positions relative to the amine. However, from 50 to 100 wt %, e.g., 70 to 100 wt %, 80 to 100 wt % or 90 to 100 wt % of all hydroxydiarylmines present in the lubrication oil composition of the invention are alkylated 3-hydroxydiphenylamines of formula I. In many embodiments, non-hydroxyl bearing alkylated diarylamines are also present in the lubricating oil composition.

DESCRIPTION

One embodiment of the invention provides a lubricating oil composition comprising
a) a lubricating oil, and
b) an alkylated 3-hydroxydiphenylamine of formula I.

In many embodiments, the alkylated 3-hydroxydiphenylamine of the invention is present from about 0.1 to about 5.0 wt %, e.g., from about 0.25, 0.3 or 0.5 to about 1.5, 2.0 or 3.0 wt %, based on the weight of the lubricating oil composition. Other embodiments provide a master batch or concentrate wherein the alkylated hydroxydiphenylamine is present in greater amounts, for example from greater than 5 to 50 wt %, such as from 7 to 40 wt %, or from 10 to 35 wt %.

Alkylated 3-hydroxydiphenylamines of the invention are compounds of formula I:

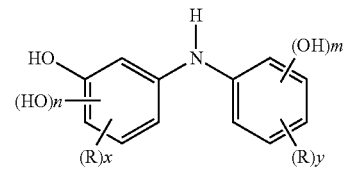

wherein n is 0 or 1; m is 0, 1 or 2; e.g., n is 0 and m is 0 or 1;

x is 0, 1 or 2 and y is 1, 2 or 3; e.g., x is 0 or 1 and y is 1 or 2;

each R is independently $C_{4-24}$, $C_{4-18}$ or $C_{4-12}$ alkyl, $C_{7-18}$ aralkyl, or $C_{4-24}$, $C_{4-18}$ or $C_{4-12}$ alkyl substituted by one or more hydroxyl and/or interrupted by one or more oxygen atom, or two adjacent R groups together with the carbons to which they are attached form a 5 to 8 member heterocyclic ring or a 6 to 8 member non-aromatic carbocyclic ring, which non-aromatic carbocyclic or heterocyclic ring is optionally substituted by alkyl, e.g., $C_{1-4}$ alkyl, hydroxyl or alkoxy;

and wherein at least one carbon atom adjacent to the amine nitrogen is unsubstituted, i.e., is substituted by hydrogen.

When two adjacent R groups together with the carbons to which they are attached form a 5 to 8 member heterocyclic ring, the heterocyclic ring may be aromatic or non-aromatic and typically comprises a nitrogen, oxygen or sulfur atom.

In many embodiments each R is independently $C_{4-24}$, $C_{4-18}$ or $C_{4-12}$ alkyl (i.e. alkyl unsubstituted by hydroxyl and uninterrupted by oxygen), or two adjacent R groups together with the carbons to which they are attached form a 6 to 8 member non-aromatic carbocyclic ring, which ring is optionally substituted by $C_{1-4}$ alkyl; for example, two adjacent R groups may form a non-aromatic 6 membered ring on a compound of formula I forming a tetrahydronaphthyl ring system as in:

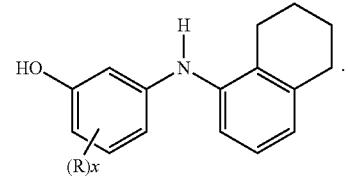

Frequently, R is $C_4$-24, $C_{4-18}$ or $C_{4-12}$ alkyl.

R as alkyl is a straight chain, branched chain, cycloalkyl or substituted cycloalkyl having the specified number of carbons and includes e.g., butyl, pentyl, hexyl, heptyl, octyl, nonyl, decyl, undecyl, dodecyl, tetradecyl, hexadecyl, octadecyl, icosane, docosant, tetracosane etc., and isomers thereof, including, as non-limiting branched alkyl examples, iso-butyl, sec-butyl, tert-butyl, iso-amyl, tert-amyl, methyl hexyl, ethyl hexyl, t-octyl, methyloctyl, ethylheptyl, propylhexyl, dimethylbutyl, dimethyheptyl, trimethylhexyl, tetramethylpentyl, ethylmethylhexyl, ethyl dimethyl pentyl, diethyl pentyl, isopropylhexyl, and the like.

In the present application, "alkyl" in general relates to straight chain, branched chain, or cyclic alkyl. Unless otherwise specified, terms such as "octyl" or "nonyl" and the like relate to a straight or branched chain alkyl. The above descriptions incorporate the term "and isomers thereof" as a formal acknowledgement of this and in order to avoid confusion. It is noted that many reactions used to alkylate an aromatic ring make use of oligomers formed from smaller olefins, such as propylene trimers, tetramers or pentamers, and the alkyl substituents formed therefrom are referred to herein as nonyl, dodecyl and pentadecyl.

R as $C_{7-18}$ aralkyl is a straight or branched chain alkyl substituted by phenyl or naphthyl, which phenyl or naphthyl may be further substituted by alky, wherein the total number of carbon atoms is from 7 to 18 and includes, e.g., benzyl, 1 or 2-phenethyl, cumyl, 1, 2 or 3-phenyl propyl, butylphenethyl, and the like.

R as alkyl interrupted by one or more oxygen atom is an ether or polyether of the specified number of carbons, wherein the alkyl segments may be straight chain, branched chain, cycloalkyl or substituted cycloalkyl, e.g., ethoxyethyl, propoxypropyl, butoxybutyl, hexyloxyhexyl, tert-butoxypropyl, tert-butoxybutyl, 2-ethylhexyloxyethyl and the like, a polyalkylene ether presented by the general formula R'O(R'O)$_n$R", wherein each R' is independently $C_{2-6}$ alkylene, R" is $C_{2-6}$ alkyl, and n is a number of from 1 to 12, provided that the total number of carbons is from 4 to 24, 4 to 18, or 4 to 12.

Often, both n and m in formula I are 0 and the 3-hydroxydiphenylamines of the invention are compounds of formula II:

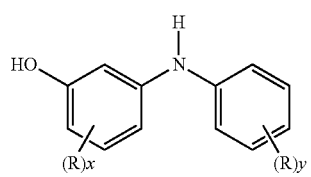

wherein R, x and y are as described above. In some embodiments, the 3-hydroxydiphenylamine of the invention is a diphenylamine of formula II wherein x is 0 or 1, and y is 1 or 2.

In select embodiments of the invention, the total number of carbon atoms of the combined groups R is at least 12, e.g., 16, 18 or higher, and in certain embodiments, the total number of carbon atoms of the combined groups R is 20 or higher, and generally in such select embodiments R is not substituted by hydroxyl or interrupted by oxygen atoms. Frequently, but not always, in these select embodiments, both aryl groups will be alkylated. Examples include, but are not restricted to, compounds of formula II wherein:

x is 0, y is 1 and R is dodecyl, octadecyl, or icosane;

x is 1, y is 1 and R is selected from hexyl, octyl, nonyl, decyl, dodecyl, or octadecyl;

x is 1, y is 1 and one R is n-butyl, sec-butyl, tert-butyl or hexyl and the other R is octyl, nonyl, or dodecyl.

Many commercial diarylamine antioxidants comprise mixtures of compounds, e.g., mixtures of mono- and di-alkylated diphenylamines, positional isomers formed by alkylation at different ring carbons, compounds with homologous alkyl substituents due to the ready availability of alkylating agents comprising homologues, different levels of branching, different positions of the double bond etc. The commercial mixtures of diaryl amines are often the result of synthetic methods or the use of less expensive stating materials comprising mixtures, but there are often advantages in using a mixture of compounds, e.g., mixtures are more likely to be liquids.

While individual compounds of formula I are described herein, many effective antioxidants of the present invention are mixtures of diarylamines comprising one or more compounds of formula I. For example, 3-hydroxydiphenyl amine can be alkylated using one or more olefins, and depending on alkylation conditions different products may be formed. Example 12 is a mixture of different mono-substituted isomers prepared by alkylation of 3-hydroxydiphenylamine with propylene trimer using a clay catalyst:

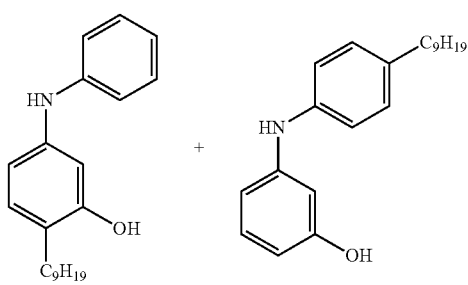

Example 13 provides a mixture of mono-substituted isomers and a di-substituted compound prepared by alkylation of 3-hydroxydiphenylamine with 2,4,4-trimethyl-1-pentene:

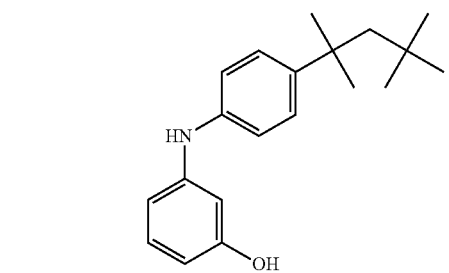

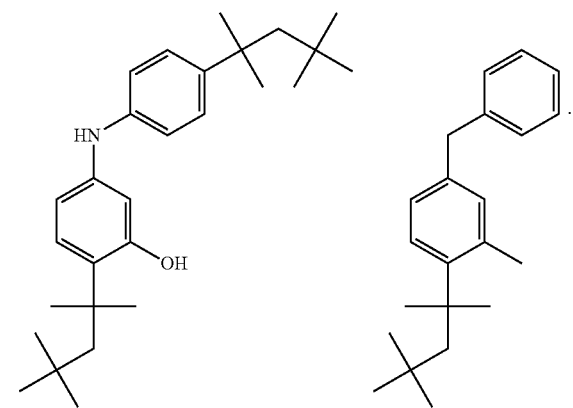

On the other hand, Example 11 provides mainly a single diarylamine by the reaction of dodecyl aniline with resorcinol:

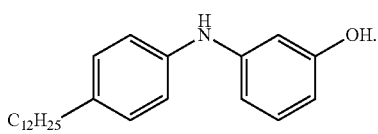

Thus, individual alkylated 3-hydroxydiphenylamines of the invention, mixtures comprising alkylated 3-hydroxydiphenylamines of the invention, or mixtures comprising one or more alkylated 3-hydroxydiphenylamines of the invention plus hydroxydiphenylamines not of formula I, can be prepared directly by appropriate selection of starting materials and reaction conditions.

Other optional additives as known in the art may be present in the present lubricating oil composition. For example, commercial lubricant formulations typically contain a variety of other additives, for example, dispersants, detergents, corrosion/rust inhibitors, other antioxidants including amine, phenol or phosphorus antioxidants, anti-wear agents, anti-foamants, friction modifiers, seal swell agents, demulsifiers, V.I. improvers, pour point depressants, and the like. A sampling of these additives can be found in, for example, U.S. Pat. Nos. 5,498,809 and 7,696,136, the relevant portions of each disclosure is incorporated herein by reference, although the practitioner is well aware that this comprises only a partial list of available lubricant additives. It is also well known that one additive may be capable of providing or improving more than one property, e.g., an anti-wear agent may also function as a friction modifier and/or an extreme pressure additive.

For example, in addition to the alkylated 3-hydroxydiphenylamines of the invention, other diarylamines may be present such as alkyldiarylamines, other hydroxydiarylamines, alkoxydiarylamines, and the like, for example, the lubricating oil composition of the invention may also contain one or more alkylated diphenylamines, many of which are commercially available The lubricant compositions of this invention will generally contain the one or more alkylated 3-hydroxydiphenylamine along with other additives in a combined concentration ranging from about 0.5 to about 30 weight percent, e.g., from about from about 1 to about 10 weight percent based on the total weight of the oil composition. For example, in some embodiments the combined additives are present from about 1 to about 5 weight percent.

In other embodiments, the composition is a master batch or concentrate, wherein the alkylated 3-hydroxydiphenylamine plus other additives are present in a total concentration ranging from 10 to 80 wt %, e.g., 20 to 80 or 30 to 70 wt % based on the weight of the master batch or concentrate.

In one particular embodiment the lubricating oil comprises one or more hydrocarbon base stocks. In other embodiments other types of base stocks and mixtures of various types of base stocks are used.

The following table shows the results of standard TEOST deposit formation testing and standard PDSC oxidation onset testing of lubricating oil compositions comprising a commercial grade hydrocarbon engine oil and 1.5 wt % of various alkylated hydroxydiphenylamines including 4-hydroxydiaphenlamines, i.e., compounds from Examples 3 and 4; 3-hydroxydiphenylamines, i.e., compounds from Examples 5, 6 and 7; and 2-hydroxydiphenylamines, i.e. from Examples compounds 8 and 9. Also shown are the results obtained from a lubricating oil composition comprising 1.5 wt % of NAUGALUBE 438L as a standard formulation.

The TEOST data is in mg of deposits, a lower value means less deposits, and the PDSC data is in minutes until onset of oxidation, a higher value represent greater protection. Compounds 5 and 6 are examples of the inventive compounds.

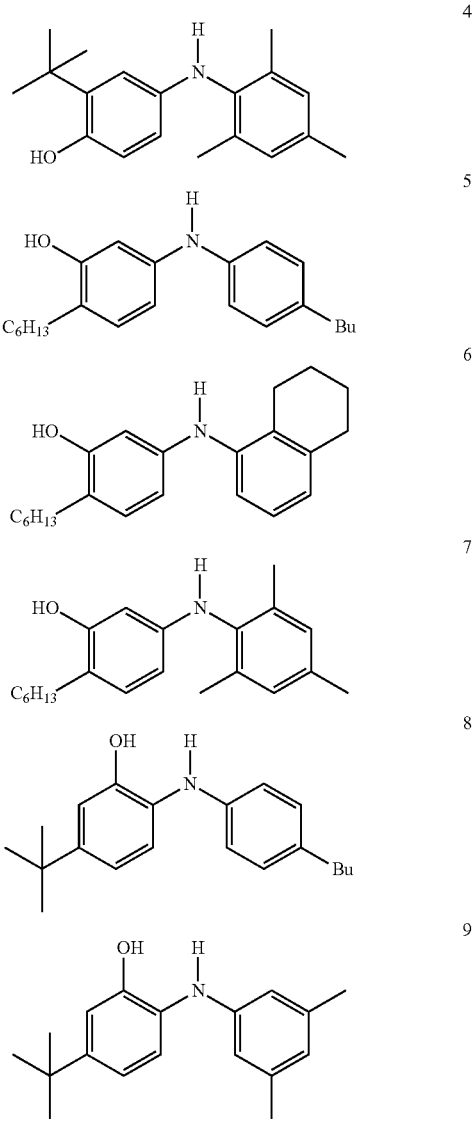

| TEOST/PDSC results at 1.5 wt % additive | | |
|---|---|---|
| Diarylamine | TEOST | PDSC |
| 438 L Standard | 50.8 | 18.6 |
| Ex 4 Comparative | 85.3 | 4.3 |
| Ex 5 | 47.6 | 12.3 |
| Ex 6 | 37.4 | 13.0 |
| Ex 7 Comparative | 31.4 | 6.7 |
| Ex 8 Comparative | 24.6 | 10.7 |
| Ex 9 Comparative | 44.0 | 6.1 |

During initial testing, it was discovered that many of the hydroxydiphenylamines of the invention showed a greater performance variance with load level than the commercial standard NL 438L. The following table lists data from another series of tests at concentrations of 1, 2 and 3 wt % of compounds from examples 10, 11 and 12 vs the standard NL 438L.

10

$C_{12}H_{25}$ — phenyl — NH — phenyl — OH (with hexyl chain)

11

$C_{12}H_{25}$ — phenyl — NH — phenyl — OH

12

HN-phenyl / $C_9H_{19}$-phenyl-NH-phenyl-OH ($C_9H_{19}$) + HN-phenyl-$C_9H_{19}$ / phenyl-OH

|  | TEOST | | | PDSC | | |
| --- | --- | --- | --- | --- | --- | --- |
|  | 1 wt % | 2 wt % | 3 wt % | 1 wt % | 2 wt % | 3 wt % |
| 10 | >60 | 31.1 | 6.4 | 5.1 | 10.5 | 19.5 |
| 11 | 56.6 | 13.6 | 9.4 | 18 | 32.3 | 46.6 |
| 12 | >60 | 33 | — | 15 | 30 | ~44 |
| 438 | >60 | 44.1 | 20.7 | 11.1 | 14.5 | 26.6 |

The lubricating oil of the invention can be any suitable oil of lubricating viscosity as described for example in co-pending U.S. application Ser. No. 12/371,872, the relevant portions of which are incorporated herein by reference. For example, a lubricating oil base stock is lubricating oil base stock, or mixtures thereof, having a kinematic viscosity at 100° C. of about 2 to about 200 cSt, about 3 to about 150 cSt, and often about 3 to about 100 cSt. Suitable lubricating oil base stocks include, for example, mineral oils such as those derived from petroleum, oils derived from coal or shale, animal oils, vegetable oils and synthetic oils. The relevant portions of co-pending U.S. application Ser. No. 12/371,872 are incorporated herein by reference.

Synthetic oils include hydrocarbon oils and halo-substituted hydrocarbon oils, such as polymerized and interpolymerized olefins, gas-to-liquids prepared by Fischer-Tropsch technology, alkylbenzenes, polyphenyls, alkylated diphenyl ethers, alkylated diphenyl sulfides, as well as their derivatives, analogs, homologs, and the like. Synthetic lubricating oils also include alkylene oxide polymers, interpolymers, copolymers, and derivatives thereof, wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from monocarboxylic acids or diacids and polyols and polyol ethers. Other esters useful as synthetic oils include those made from copolymers of alphaolefins and dicarboxylic acids which are esterified with short or medium chain length alcohols.

The synthetic oils may comprise at least one of an oligomer of an α-olefin, an ester, an oil derived from a Fischer-Tropsch process, and a gas-to-liquid stock. Synthetic base stock lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1 octenes), poly(1-decenes)); alkylbenzenes (e.g., dodecylbenzenes, tetradecylbenzenes, dinonylbenzenes, di(2-ethylhexyl)benzenes); polyphenyls (e.g., biphenyls, terphenyls, alkylated polyphenols); and alkylated diphenyl ethers and alkylated diphenyl sulfides and derivative, analogs, and homologs thereof.

Silicon-based oils, such as the polyalkyl-, polyaryl-, polyalkoxy-, or polyaryloxy-siloxane oils and silicate oils, comprise another useful class of synthetic lubricating oils. Other synthetic lubricating oils include liquid esters of phosphorus-containing acids, polymeric tetrahydrofurans, poly alphaolefins, and the like.

Lubricating oil base stocks derived from the hydroisomerization of wax may also be used, either alone or in combination with the aforesaid base stocks. Such wax isomerate oil is produced by the hydroisomerization of waxes or mixtures thereof over a hydroisomerization catalyst. Natural waxes are typically the slack waxes recovered by the solvent dewaxing of mineral oils; synthetic waxes are typically the waxes produced by the Fischer-Tropsch process.

In many embodiments, the oil base stock comprises mineral oils. For example, the lubricating oil of the invention may be a petroleum oil, or a mixture comprising a petroleum oil. Many other embodiments include vegetable oils, paraffinic oils, naphthenic oils, aromatic oils, and derivatives thereof, often as combination of base stocks.

Useful base stocks from vegetable and animal sources include, for example, alkyl esters of fatty acids, which include commercial mixtures of the ethyl, propyl, butyl and especially methyl esters of fatty acids with 12 to 22 carbon atoms. For example, lauric acid, myristic acid, palmitic acid, palmitoleic acid, stearic acid, oleic acid, elaidic acid, petroselic acid, ricinoleic acid, elaeostearic acid, linoleic acid, linolenic acid, eicosanoic acid, gadoleic acid, docosanoic acid, or erucic acid are useful and have an iodine number from 50 to 150, especially 90 to 125. Mixtures with particularly advantageous properties are those which contain mainly, i.e., at least 50 wt. %, methyl esters of fatty acids with 16 to 22 carbon atoms and 1, 2, or 3 double bonds. The preferred lower alkyl esters of fatty acids are the methyl esters of oleic acid, linoleic acid, linolenic acid, and erucic acid.

Often the base stock of lubricating viscosity can comprise a Group I, Group II, or Group III base stock or base oil blends of the aforementioned base stocks, for example, the oil of lubricating viscosity is a Group II or Group III base stock, or a mixture thereof, or a mixture of a Group I base stock and one or more of a Group II and Group III. Generally, a major amount of the oil of lubricating viscosity is a Group II, Group III, Group IV, or Group V base stock, or a mixture thereof. The base stock, or base stock blend, typically has a saturate content of at least 65%, e.g., at least 75% or at least 85%. Most preferably, the base stock, or base stock blend, has a saturate content of greater than 90%.

Definitions for the base stocks and base oils in this invention are the same as those found in the American Petroleum Institute (API) publication "Engine Oil Licensing and Certification System," Industry Services Department (14th ed., December 1996), Addendum 1, December 1998. This publication categorizes base stocks as follows.
  (a) Group I base stocks contain less than 90 percent saturates (as determined by ASTM D 2007) and/or greater than 0.03 percent sulfur (as determined by ASTM D 2622, ASTM D 4294, ASTM D 4927 and ASTM D 3120) and have a viscosity index greater than or equal to 80 and less than 120 (as determined by ASTM D 2270).
  (b) Group II base stocks contain greater than or equal to 90 percent saturates (as determined by ASTM D 2007) and less than or equal to 0.03 percent sulfur (as determined by ASTM D 2622, ASTM D 4294, ASTM D 4927 and ASTM D 3120) and have a viscosity index greater than or equal to 80 and less than 120 (as determined by ASTM D 2270).
  (c) Group III base stocks contain greater than or equal to 90 percent saturates (as determined by ASTM D 2007) and less than or equal to 0.03 percent sulfur (as determined by ASTM D 2622, ASTM D 4294, ASTM D 4927 and ASTM D 3120) and have a viscosity index greater than or equal to 120 (as determined by ASTM D 2270).
  (d) Group IV base stocks are polyalphaolefins (PAO).
  (e) Group V base stocks include all other base stocks not included in Groups I-II, III, or IV.

The lubricating oil compositions of the invention can be used in a variety of applications, for example, crankcase lubricating oils for spark-ignited and compression-ignited internal combustion engines, gas engine lubricants, wind turbine lubricants, automatic transmission fluids, gear lubricants, compressor lubricants, metal-working lubricants, hydraulic fluids, and other lubricating oil and grease compositions.

EXAMPLES

In the following examples, aniline, basic alumina, 4-butylaniline, 4-tert-butylcatechol, catechol, 4-hexylresorcinol, resorcinol, 5,6,7,8-tetrahydronaphthylamine, and triphenyl phosphite were obtained from Sigma-Aldrich Chemical Company. 3-hydroxydiphenylamine is available from TCI. Dodecylaniline (branched) is available from Dottikon Exclusive Synthesis AG. Propylene trimer is available from Shell Chemical Company. Nonylaniline may be prepared by alkylation of aniline with propylene trimer.

Example 1:
4-hydroxy-3-tert-butyl-4'-butyldiphenylamine

A 1:1 molar ratio of 4-butylaniline and tert-butylhydroxyquinone was heated at 220-240 C in the presence of 6 wt % triphenylphosphite, based on the weight of tert-butylhydroxyquinone, for approximately 8 hours to yield the crude product as a solid which was melted, stirred in the presence of a 5% ethyl acetate/hexane mixture at 60 C, which mixture was cooled to room temperature and silica gel was added. The mixture was stirred then filtered and filtrate was subjected to distillation to provide the product.

Example 2-9

Using a procedure similar to that of Example 1, a series of alkylated hydroxydiarylamines was prepared from aniline and dihydroxybenzene derivatives as shown in Table 1.

TABLE 1

| Product of Example | | aniline derivative | dihydroxybenzene derivative |
|---|---|---|---|
| 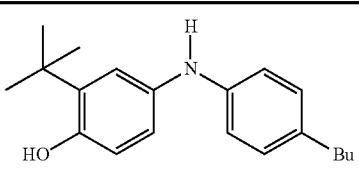<br>1 Comp | | 4-butylaniline | tert-butylhydroxyquinone |
| 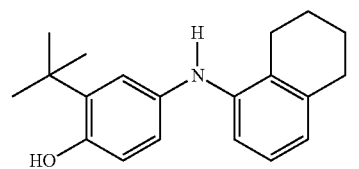 [SMILES: CC(C)(C)c1cc(Nc2cccc3c2CCCC3)ccc1O]<br>2 Comp | | 5,6,7,8-tetrahydronaphthylamine | tert-butylhydroxyquinone |
| 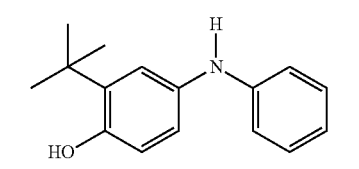 [SMILES: CC(C)(C)c1cc(Nc2ccccc2)ccc1O]<br>3 Comp | | aniline | tert-butylhydroxyquinone |

TABLE 1-continued

| Product of Example | aniline derivative | dihydroxybenzene derivative |
|---|---|---|
| 4 Comp | 2,4,6-trimethylaniline | tert-butylhydroxyquinone |
| 5 | 4-butylaniline | 4-hexylresorcinol |
| 6 | 5,6,7,8-tetrahydronaphthylamine | 4-hexylresorcinol |
| 7 Comp | 2,4,6-trimethylaniline | 4-hexylresorcinol |
| 8 Comp | 4-butylaniline | 4-tert-butylcatechol |
| 9 Comp | 3,5-dimethylaniline | 4-tert-butylcatechol |

Results from TEOST and PDSC testing at 1.5 wt % loadings are shown in Table 2 for compounds 3-9 alone and in mixtures with NAUGALUBE 438L.

TABLE 2

TEOST/PDSC results at 1.5 wt % additive

| Diarylamine | Single Diarylamine | | Mixture w/ 50% NL 438L | |
|---|---|---|---|---|
| | TEOST | PDSC | TEOST | PDSC |
| 438 L Standard | 50.8 | 18.6 | — | — |
| 3 Comparative | 95.3 | 4.0 | 56.9 | 13.0 |
| 4 Comparative | 85.3 | 4.25 | — | — |
| 5 | 47.6 | 12.25 | 25.3 | 19.5 |
| 6 | 37.4 | 13.0 | 16.4 | 23.6 |
| 7 Comparative | 31.4 | 6.7 | 28.5 | 14.5 |
| 8 Comparative | 24.6 | 10.7 | 18.5 | 14.5 |
| 9 Comparative | 44.0 | 6.13 | 33.15 | 10.51 |

Examples 10-14

Structures of the products for examples 10-14 are found in Table 3 along with results from PDSC and TEOST testing at 2 wt % loading.

Example 10

A 50 mL three-neck flask equipped with an overhead stirrer, thermocouple, and a Dean-Stark trap topped by a spiral condenser was charged with 16.7 g dodecyl aniline, 10.3 g 4-hexylresorcinol, and 0.8 g p-toluene sulfonic acid. The reaction was stirred at 203° C. for 4 h. The product was taken up in xylenes, extracted with aqueous sodium bicarbonate, and washed with water. Volatiles were removed by rotary evaporation, followed by vacuum distillation to yield the product as a dark orange oil.

Example 11

A 50 mL three-neck flask equipped with an overhead stirrer, thermocouple/nitrogen inlet, and short path distillation condenser was charged with 17.2 g dodecyl aniline, 7.3 g resorcinol, and 4.5 g basic alumina. The reaction was stirred at 220° C. for 20 h. An additional 3.3 g basic alumina was added, and the reaction was stirred at 220° C. for 7 h. An additional 3.6 g resorcinol was added, and the reaction at 220° C. for 28 h. The reaction mass was taken up in ethyl acetate and filtered through diatomaceous earth. Volatiles were removed by rotary evaporation followed by vacuum distillation to yield the product as a viscous dark red liquid.

Example 12

A 250 mL four-neck flask equipped with an overhead stirrer, thermocouple, spiral condenser and addition funnel was charged with 30 g 3-hydroxydiphenylamine, 5.8 g Filtrol 20× (oven dried 3 h at 150° C.) and 21.5 g propylene trimer. The reaction was heated to 140° C., and maintained at that temperature throughout the reaction. Additional propylene trimer (23.9 g) was added dropwise in two parts over 7 h, and the reaction was stirred for 4 h. A further 22.1 g propylene trimer was added dropwise in two parts over 8 h. A final 22.9 g propylene trimer was added dropwise in two parts over 5 h., and the reaction was stirred for an additional 5.5 h. The reaction mass was filtered through diatomaceous earth, and the filter pad rinsed with ethyl acetate. Volatiles were removed by rotary evaporation followed by vacuum distillation to yield the product as a clear light brown viscous oil.

Example 13

A 50 mL three-neck flask equipped with an overhead stirrer, a thermocouple and a 13 cm dry ice condenser (with septum, nitrogen inlet and a polyethylene needle reaching to the reaction), was charged with 12.6 g 3-hydroxydiphenylamine and 3.7 g Filtrol 20× (oven dried 3 h at 150° C.). The reaction was held at 138° C. while 2,4,4-trimethyl-1-pentene (31 mL) was added steadily over 23 h. The reaction mixture was diluted with ethyl acetate and filtered through diatomaceous earth. Volatiles were removed by rotary evaporation followed by vacuum distillation to yield the product as dark brown solid containing a 74:12:4 mixture of 3-hydroxy-4'-(1,1,3-3-tetramethylbutyl)diphenylamine: 3-hydroxy-4,4'-bis(1,1,3-3-tetramethylbutyl) diphenylamine: 3-hydroxy-4-(1,1,3-3-tetramethylbutyl)diphenylamine.

Example 14

A 100 mL three-neck flask, equipped with an overhead stirrer, a Claisen head with a thermocouple and nitrogen inlet, and a short-path distillation apparatus was charged with 17.6 g 4-hexylresorcinol, 19.8 g nonylaniline, and 10.8 g basic alumina. The reaction was stirred at 220° C. for 41 h, then cooled. An additional 5.1 g basic alumina was added, and the reaction was stirred at 220° C. for 7 h. Temperature was increased to 232° C. for 18 h. The reaction mixture was taken up in ethyl acetate/hexanes and centrifuged. The supernatant was filtered through diatomaceous earth, and solvent was removed by rotary evaporation. Unreacted starting material was removed by vacuum distillation to yield 22.3 g clear orange liquid.

TABLE 3

| Product of Example | TEOST 2 wt % | PDSC 2 wt % |
|---|---|---|
| NAUGALUBE 438 L Standard | 44.1 | 16.2 |
| 10 (structure shown) | 31.1 | 10.5 |

10

TABLE 3-continued
| Product of Example | TEOST 2 wt % | PDSC 2 wt % |
|---|---|---|
| 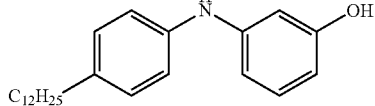 11 | 13.6 | 32.3 |
| 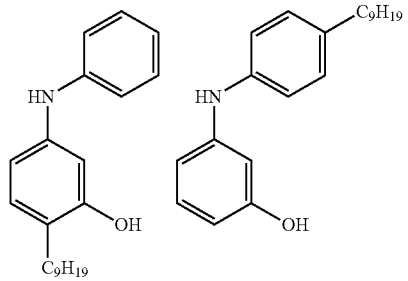 12 | 33.1 | 38 |
| 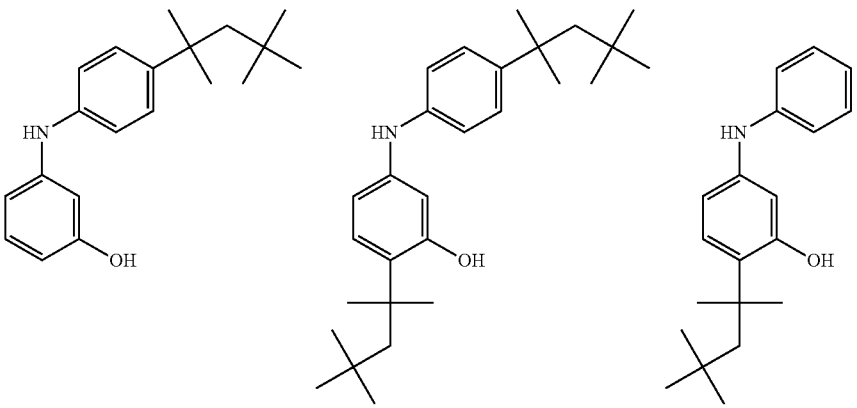 [SMILES: CC(C)(C)CC(C)(C)c1ccc(Nc2cccc(O)c2)cc1 ; CC(C)(C)CC(C)(C)c1ccc(Nc2ccc(C(C)(C)CC(C)(C)C)c(O)c2)cc1 ; CC(C)(C)CC(C)(C)c1ccc(Nc2ccccc2)cc1O] 13 | 29.4 | 37 |
| 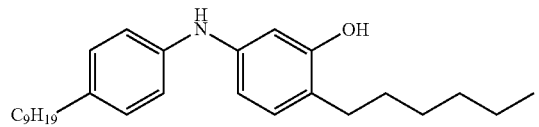 14 | | |

Deposit control (TEOST) and oxidation induction (PDSC or RPVOT) results at 3 wt % loadings are shown below for compound 11 and 10 alone and in mixtures with NAUGALUBE 438L, NAUGALUBE APAN (alkylated phenyl naphthyl amine) or NAUGALUBE 531 (hindered phenol).

| TEOST/PDSC results at 3 wt % Additive | | | | | |
|---|---|---|---|---|---|
| | Single Diarylamine | | * Mixture w/50% NL 438L | | 25% NL 438L/ 75% Inventive Ex |
| | TEOST | PDSC | TEOST | PDSC | TEOST | PDSC |
| 438L Standard | 20.7 | 26.7 | — | — | — | — |
| Ex 11 | 9.4 | 46.6 | 6.8 | 46.6 | 9.3 | 52.5 |
| Ex 10 | 6.4 | 19.5 | 10.6 | 30 | — | — |

* 1.5% N-438L plus about 1.5% of the experimental, with the exact charge of experimental adjusted to have a Nitrogen content equal to 3% N-438L.

| TEOST/PDSC results at 3 wt % Additive | | | | | |
|---|---|---|---|---|---|
| | Single Compound | | Mixture w/50% NL APAN | | Mixture w/50% NL 531 |
| | TEOST | PDSC | TEOST | PDSC | TEOST | PDSC |
| NL APAN | 16.3 | 22.1 | — | — | — | — |
| NL 531 | 50.2 | — | 10.2 | — | — | — |
| Ex 11 | 9.4 | 46.6 | 10.4 | 39.4 | 21.3 | — |
| EX 10 | 6.4 | 19.5 | 8.6 | 27 | 13.5 | |

| Oxidation induction time by RPVOT: | | |
|---|---|---|
| | 0.5% Single Additive | 0.25% NL 438NL/ 0.25% Example |
| N438L | 280 | — |
| Ex 11 | 770 | 1300 |
| Ex 10 | 340 | 650 |

What is claimed:

1. An alkylated 3-hydroxydiphenylamine of formula I:

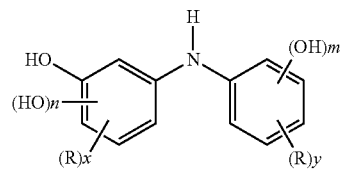

wherein n is 0 or 1; m is 0, 1 or 2;
x is 0, 1 or 2 and y is 1, 2 or 3;
each R is independently $C_{4-24}$ alkyl or $C_{4-24}$ alkyl substituted by one or more hydroxyl and/or interrupted by one or more oxygen atom,
or two adjacent R groups together with the carbons to which they are attached form a 5 to 8 member heterocyclic ring or a 6 to 8 member non-aromatic carbocyclic ring, which heterocyclic or non-aromatic carbocyclic ring is optionally substituted by alkyl, hydroxyl or alkoxy;
at least one carbon atom adjacent to the amine nitrogen is unsubstituted; and
wherein the total number of carbon atoms of the combined groups R is 12 or higher.

2. The alkylated 3-hydroxydiphenylamine according to claim 1 wherein n is 0 and m is 0 or 1.

3. The alkylated 3-hydroxydiphenylamine according to claim 2 wherein m is 0.

4. The alkylated 3-hydroxydiphenylamine according to claim 1 wherein x is 0 or 1 and y is 1 or 2.

5. The alkylated 3-hydroxydiphenylamine according to claim 1 wherein each R is independently $C_{4-24}$ alkyl, or two adjacent R groups together with the carbons to which they are attached form a 6 to 8 member non-aromatic carbocyclic ring, which ring is optionally substituted by $C_{1-4}$ alkyl.

6. The alkylated 3-hydroxydiphenylamine according to claim 1 wherein, the total number of carbon atoms of the combined groups R is 16 or higher.

7. The alkylated 3-hydroxydiphenylamine according to claim 5 wherein, the total number of carbon atoms of the combined groups R is 16 or higher.

8. A lubricating oil composition comprising
a) a lubricating oil, and
b) one or more alkylated 3-hydroxydiphenylamine according to formula I:

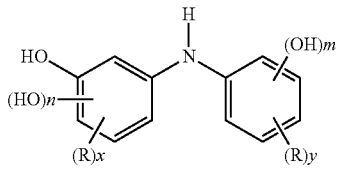

wherein n is 0 or 1; m is 0, 1 or 2;
x is 0, 1 or 2 and y is 1, 2 or 3;
each R is independently $C_{4-24}$ alkyl or $C_{4-24}$ alkyl substituted by one or more hydroxyl and/or interrupted by one or more oxygen atom,
or two adjacent R groups together with the carbons to which they are attached form a 5 to 8 member heterocyclic ring or a 6 to 8 member non-aromatic carbocyclic ring, which heterocyclic or non-aromatic carbocyclic ring is optionally substituted by alkyl, hydroxyl or alkoxy;
and wherein at least one carbon atom adjacent to the amine nitrogen is unsubstituted.

9. The lubricating oil composition according to claim 8 wherein b) is present in an amount of about 0.1 to about 5.0 wt %, based on the weight of the lubricating oil composition.

10. The lubricating oil composition according to claim 8 wherein b) is present in an amount of greater than 5 to about 50 wt %, based on the weight of the lubricating oil composition.

11. The lubricating oil composition according to claim 8 further comprising one or more non-hydroxyl bearing alkylated diarylamine.

12. The lubricating oil composition according to claim 8 wherein the lubricating oil comprises one or more hydrocarbon base stocks.

13. The lubricating oil composition according to claim 9 further comprising one or more non-hydroxyl bearing alkylated diarylamine.

14. The lubricating oil composition according to claim 9 wherein the lubricating oil comprises one or more hydrocarbon base stocks.

15. The lubricating oil composition according to claim 10 further comprising one or more non-hydroxyl bearing alkylated diarylamine.

16. The lubricating oil composition according to claim 10 wherein the lubricating oil comprises one or more hydrocarbon base stocks.

17. The lubricating oil composition according to claim 11 wherein the lubricating oil comprises one or more hydrocarbon base stocks.

18. The lubricating oil composition according to claim 13 wherein the lubricating oil comprises one or more hydrocarbon base stocks.

19. The lubricating oil composition according to claim 8, wherein in the one or more alkylated 3-hydroxydiphenylamine the total number of carbon atoms of the combined groups R is 12 or higher.

20. The lubricating oil composition according to claim 8, wherein in the one or more alkylated 3-hydroxydiphenylamine the total number of carbon atoms of the combined groups R is 16 or higher.

* * * * *